(12) United States Patent
Kastner

(10) Patent No.: US 6,552,793 B1
(45) Date of Patent: Apr. 22, 2003

(54) DETERMINATION OF THE QUALITY OF A GAS

(75) Inventor: Joachim Kastner, Dortmund (DE)

(73) Assignee: Flowcomp Systemtechnik GmbH, Dortmund (DE)

( * ) Notice: Subject to any disclaimer, the term of this patent is extended or adjusted under 35 U.S.C. 154(b) by 0 days.

(21) Appl. No.: 09/868,080

(22) PCT Filed: Oct. 11, 2000

(86) PCT No.: PCT/DE00/03572

§ 371 (c)(1),
(2), (4) Date: Jun. 14, 2001

(87) PCT Pub. No.: WO01/27595

PCT Pub. Date: Apr. 19, 2001

(30) Foreign Application Priority Data

Oct. 14, 1999 (DE) .......................... 199 49 439

(51) Int. Cl.⁷ ............................ G01N 21/00; G01J 5/02
(52) U.S. Cl. .............................. 356/437; 250/343
(58) Field of Search ............................ 250/343; 356/437

(56) References Cited

U.S. PATENT DOCUMENTS

| | | | |
|---|---|---|---|
| 3,950,101 A | 4/1976 | Dewey, Jr. .................. 356/51 |
| 4,594,510 A | 6/1986 | Brown et al. .......... 250/339.13 |
| 6,157,455 A | * 12/2000 | Pinvidic et al. ............. 356/437 |

FOREIGN PATENT DOCUMENTS

EP       0 882 977        12/1998 ................. 356/437

* cited by examiner

Primary Examiner—Georgia Epps
Assistant Examiner—David N. Spector
(74) Attorney, Agent, or Firm—Collard & Roe, P.C.

(57) ABSTRACT

A procedure for the determination of the quality of gas of a probe gas, in particular a burnable gas, using a transmission spectrum of the probe gas determined at operating conditions by means of spectroscopical methods of measurement. At least the associated values of the pressure p and the temperature T of the probe gas are determined and in a number of selected spectral regions at least one spectral vector is constituted by integrating quantities of the transmission spectrum of the probe gas, which shows as components the values of the integrals with respect to the selected spectral regions and is characteristic for the properties of the probe gas at operating conditions. Afterwards, for the determination of a physical quantity according to the quality of gas, the spectral vector is multiplied with a factor vector, which has been evaluated by means of calibrating measurements of spectral vectors of calibrating gases of known features and under known conditions of state, in which with respect to the physical quantity to be determined according to the quality of gas, a respective factor vector is brought in.

29 Claims, No Drawings

DETERMINATION OF THE QUALITY OF A GAS

CROSS-REFERENCE TO RELATED APPLICATIONS

Applicant claims priority under 35 U.S.C. §119 of German Application No. 199 49 439.8 filed Oct. 14, 1999. Applicant also claims priority under 35 U.S.C. §120 of PCT/DE00/03572 filed Oct. 11, 2000. The international application under PCT article 21(2) was not published in English.

BACKGROUND OF THE INVENTION

1. Field of the Invention

The invention concerns to a procedure for the photometric determination of the quality of gas, particularly of burning gases, according to the precharacterising part of claim 41.

2. The Prior Art

For determining the quality of gas for example in distribution networks for natural gas or the like, devices for measuring the quality of the guided-through gases are used. These devices measure the condition of gas. Natural gas, because of being a natural product according to its origin and by mixture shows respective fluctuations in respect of its composition, whereas the composition for example of natural gas coming from the different hydrocarbons determines the caloric value from extrapolated quantities. Therefore it is of great importance to measure the guided-through amount of gas in a gas supply network and therewith the respective amount of energy, to determine the exact respective condition at the feeding point into the natural gas network and at the deliverance points of the customers and therewith to deduct a definite transported or supplied amount of energy. In doing so for the customer of the gas, an invoice can always state the actual supplied amount of energy relating to different conditions of the gas and a correspondingly varying amount of energy. Vice versa, the detection of the condition of the gas offers the guarantee for the customer to obtain a desired quality and therewith a required amount of energy.

The determination of the quality of gas obtains additional relevance, since with the elimination of the guiding-through monopoly, the suppliers of natural gas use the same network for delivering gases of quite different provenance and therefore also different composition. Only an easy and cost-effective detection of the condition of the gas by means of cost-effective measuring devices and methods allows for a controllable and accurate accounting.

For the measurement of the quality of gas as relevant quantities, the standard volumetric gross calorific value $H_{v,n}$, the standard density $\rho_n$ and the compressibility coefficient K have to be determined as accurately as possible and also regarding the different gas qualities.

In practice, for the settlement of account, the transported volume Vb of the of the gas at working conditions (pressure $p_b$, temperature $T_b$) is measured by means of flow measuring devices. With knowledge of the condition of the gas, the compressibility coefficient K can be determined, with which the volume of the gas $V_n$ at standard conditions (pressure $p_n$, temperature $T_n$) is calculated.

$$V_n = \frac{p_b T_n}{p_n T_b} \frac{1}{K} V_b$$

By means of multiplication of this standard volume with the volumetric gross calorific value $H_{v,n}$ at standard conditions, the transported amount of energy Q can be obtained:

$$Q = V_n H_{v,n}$$

Alternatively, the volume at working conditions $V_b$ can directly be multiplied with the volumetric gross calorific $H_{v,b}$ at working conditions (Energymeter).

Another important quantity for applications with natural gas is the thermal output of gas burners; this varies in accordance to the gas quality and is characterized by means of the so-called Wobbe index Wv: gases with the same Wobbe index Wv deliver the same thermal output at a burner nozzle. For calculating the Wobbe index Wv the standard density $\rho_n$ of the gas is required, from which the relative density according to air is determined (dv=ρgas/ρair)

$$W_v = \frac{H_v}{\sqrt{d_v}}$$

Therefore the determination of the gross calorific value $H_{v,n}$ at standard conditions has central relevance for the practical determination of the quality of gas, for example, for accounting purposes.

Until now different devices for the measurement of the gas quality are used. So-called direct and so-called indirect procedures are known. By using direct procedures, the quantities to be determined are measured separately and therefore the gas is transformed to standard conditions, by which expensive treatments of the gas are required.

The gas condition can be determined most easily by means of so-called calorimeters, in which by means of an open flame a gas probe is burnt and submitted to a cooling medium. Heat quantity and the thereupon detectable temperature rise of the cooling medium the calorific value of the burnt gases can be determined. Such devices will need a complicated mechanic for the adjustment of a certain quantitative proportion of gas, combustion air and for example cooling air as cooling medium and are therefore expensive and error prone, and enhanced security requirements for the devices are necessary due to the open burning. Also the maintenance and calibration have to be carried out by qualified personnel, and the calorimeter must be used in conditioned rooms. Therefore the purchase and operating costs of such test assemblies are very high.

Using calorimetry by means of catalytic burning (for example with pellistors) the probe gas is mixed with air and burnt at the 400 to 500° C. hot helixes of a catalyst. The temperature rise of the catalyst is about proportional to calorific value. Because this procedure is based on a sensitive surface effect, it is subject to strong drifts and necessitates frequent calibration with search gas. The catalytic calorimeter is most favorable of all mentioned procedures, however, because it is better suited for control than for accounting because of its accuracy.

The direct measurement of the density $\rho_b$ at working conditions is done with hydrostatic balances, which are very expensive precision devices, with which the buoyancy of a ball filled with nitrogen is measured in accordance to the density of the surrounding medium, here of the probe gas. With another procedure a thin-walled metal cylinder, which is positioned by a current linkage of the probe gas, is set in oscillation. The density of the surrounding gas determines the resonant frequency of the cylinder, which is captured as a sensitive measured quantity. Both procedures are very expensive for the determination of the standard density, because you they require an adjustment to the standard conditions.

The compressibility coefficient K cannot be measured directly, but instead can be calculated by means of different numerical standard-arithmetic techniques out of the directly measurable gas quantities. One of these procedures, the so-called GERG88-procedure (DVGW-worksheet 486) needs the input quantities listed in table 1 below. The amount of substance of $CO_2$ is determined according to the state of the art by a non dispersive infrared-spectroscopical procedure (NDIR), whereby the gas must be brought into a defined condition near or at standard conditions. The amount of substance of $H_2$ is of significance only when working with coke oven gases and can be left unattended in the typical natural gases today distributed in Europe. The compressibility coefficient K can be determined to $10^{-3}$ with the help of the GERG88-equation in case of sufficient accuracy of the input quantities.

TABLE 1

| input quantities of the GERG88-procedure | |
|---|---|
| $P_b$ | pressure at working conditions |
| $T_b$ | temperature at working conditions |
| $\rho_n$ | density at standard conditions |
| $H_{v,n}$ | volumetric gross calorific at standard conditions |
| $xCO_2$ | amount of substance of $CO_2$ |
| $xH_2$ | amount of substance of $H_2$ |

The other procedure for determination of the behavior of real gases is done according to the AGA8-92DC-equation (ISO 12213-2:1997 (E)). This process requires as input quantities the amount of substance of 21 leading gas components (table 2) and has an accuracy of $10^{-3}$.

TABLE 2

| input quantities of the AGA8-92DC-equation | |
|---|---|
| methane | $CO_2$ |
| ethane | $N_2$ |
| propane | $H_2S$ |
| isobutane | He |
| n-butane | $H_2O$ |
| isopentane | $O_2$ |
| n-pentane | Ar |
| n-hexane | $H_2$ |
| n-heptane | CO |
| n-octane | pressure |
| n-nonane | temperature |
| - decyl hydride | |

The state of the technology includes, besides the direct measurement techniques, also the indirect measurement of the gas quality by means of gas chromatography. A defined volume of the probe gas is brought into a defined condition and is carried by a carrier gas, typically helium, through a system of gaschromatographic separation columns. Due to their different retention times, the individual gas components reach the downstream sensor, generally this is a detector for caloric conductibility, at the end of the separation column at different times. The peak area of the sensor signal can therefore be interpreted as amount of substance, whereas the evaluation must be carried out in comparison with a reference gas, that must have a similar composition to the probe gas.

The drawback of the gas chromatography is the expensive sample preparation and installation of the whole system, and the expensive maintenance and operation by well-trained personnel. From the amounts of substances of the individual gas components that the gas chromatography delivers, all relevant gas quantities can be calculated. For the implementation of such indirect measurements via chromatography, automatically working process chromatographs with detectors for caloric conductability are deployed. These devices generally measure eleven components of the natural gas ($N_2$, $CO_2$, $CH_4$, $C_2H_6$, $C_3H_8$, $C_4H_{10}$, $C_5H_{12}$, $C_6+$ and so on) Helium is used as the carrier gas, but its light volatility in practice often leads to prematurely emptying of the bottle for the carrier gas and therefore leads to short maintenance cycles for such a device. A gas is chosen as the calibrating gas that is similar to the natural gas to be measured.

Such chromatographic systems carry out measurement cycles without interruption, in order to capture changes in the quality of the gas immediately. This leads to a high consumption of carrier gas and calibrating gas and requires that maintenance of the device be performed in relatively short intervals.

It is also known to determine the composition of a gas with conventional infra-red-gas-analyzers. Such analyzers working in the middle infra-red or near infra-red area do not offer the requirements of high precision and stability for a determination of the caloric value under the measurement conditions which are required here.

Also, a parallel reference measurement must be carried out beside the intrinsic measurement of the probe gas, for the sake of compensating the at least essential influences of failures. As a measuring result, the known infra-red-gas analyzers deliver superimposed frequency spectrums, that make it very difficult to form a conclusion regarding individual components of a inspected gases.

In the literature there has been described an infrared spectroscopical procedure for gas analysis (Optical BTU sensor Development," Gas Research Institute GRI-93/0083), that determines by means of-so-called multivariate analysis (MVA) of the near infrared spectrum of gases the volumetric concentration of the amount of substances of the carbon-containing components of the gas and therewith of the volumetric caloric value under operating conditions. This procedure does not deliver the calorific value $H_{v,n}$ under standard conditions or the standard reference density $\rho_n$ and the amount of substance of $CO_2$, so that it is not qualified for the determination of the compressibility coefficient K nor the complete determination of the quality of a gas. Determining the calorific value by means of known photometric methods requires necessary equipment for the realization of the procedures, whereby a benefit in the speed of the coverage of the absorption spectrums of the natural gas in near or middle infrared spectral area is obtained. The entire absorption spectrum of the natural gas is therefore put together from of the sum of single spectrums of components represented in gas and therefore can be measured and analyzed with the aid of more appropriate methods of spectral analysis.

Doing this, the ascertained quota of extinction of a component in the entire spectrum of the natural gas is equivalent to the part of the concentration of this component within search gas (so-called Beer-Lambert-law). With the knowledge of the calorific value of this respective component, the calorific value of the entire mixture of gases can then be calculated as a summation value. This procedure of spectral analysis has the problem, however, of the intense overlap by absorption bands of different components, which frequently lead to inaccurate results and beyond that to a high calculation effort. One more infrared spectroscopical procedure according to DE 198 38 301 A1 acts as a direct spectral evaluation (DSA) with a spectral function, with which the spectrum of the gas is folded. The procedure allows the specification of the volumetric calorific value $H_{v,b}$ under operating conditions direct from the spectrum. While burning the gas, the respectively caused heat of the reaction is based on the combustion of C—H-bindings and a thereby caused heat quantity depends to the present binding energy. This is thereby exploited, that the oscillations of the C—H-bindings, which are equal to each other, have a certain binding energy and produce the same heat quantity during a combustion, interact with an associated wavelength of an electromagnetic radiation. It is possible by means of a wavelengths-resolved measuring and a wavelengths-dependent valence of the grade of interaction of these oscillations to calculate the calorific value $H_{v,b}$ of the gas, without the requirement of an identification of individual gas components. This document additionally discloses a device for the realisation of such a procedure, which is tuned for the specific requirements of the measuring method and enables a weighted summing up of the grades of interaction. With this procedure, the calorific value $H_{v,b}$ of a mixture of gases under operating conditions can be determined, the other quantities relating to the determination of gas quality can itself not be determined with measuring techniques.

It is further known a procedure according to DE 199 00 129.4 A1, in which the density of a probe gas at working conditions is determined with an optical-spectroscopical procedure. This procedure proceeds on the assumption, that each binding of the IR-active gas components contributes to the extinction, whereby with each binding the mass of the coupled atoms is associated. In this manner, the mass of all the IR-active atoms is represented by contributions to absorption within the spectrum. The frequency of oscillation of each binding and therewith its spectral location depends on the reduced mass of the partners of binding. The spectrum contains in its amount and its spectral distribution information for determination of the density of the gas. The context between the spectrum and the mass in the measuring volume and therewith with the density at working conditions of the gas is described by a spectral weighting function, which can be called spectral density. The contribution of masses of the IR-inactive components will be calculated via the stated quantities and an appropriate formulation for the compressibility behaviour. In such a procedure, multiple iterations are required, for which certain assumptions with regard to the initial conditions must be taken, which possibly can be problematic with regard to the convergence of the iteration.

SUMMARY OF THE INVENTION

Therefore, it is object of the present invention to suggest a procedure for the determination of the quality of gas, with which the quantities relevant for the quality of gas can be determined by means of a spectroscopical detection of the quality of gas, as well as respective evaluations. The invention comprises a procedure for the determination of the quality of a probe gas, in particular a burnable gas, in which at operating conditions by means of spectroscopical methods of measurement a transmission spectrum of the probe gas is determined. In a first step, at least the associated values of the pressure p and the temperature T of the probe gas are determined. In a further step, in a number of selected spectral regions at least one spectral vector is created by integrating quantities of the transmission spectrum of the probe gas. The spectral vector has as components the values of the integrals with respect to the selected spectral regions and which are characteristic for the properties of the probe gas at operating conditions. In a further step, a physical quantity to be determined in that spectral vector is multiplied with a factor vector. The factor vector has been evaluated by calibrating measurements of spectral vectors of calibrating gases having known features and under known conditions, in which in respect to the physical quantity to be determined a respective factor vector is brought in. In this way, the physical quantity to be determined according to the quality of gas is measured directly by inclusion of the state of the probe gas by evaluating the spectrum and without iteration. By connecting the data for the pressure p and the temperature T derived out of the measuring of the state of the probe gas with the spectral vector, which is derived out of the transmission spectrum, the quantities of the probe gas at operating conditions can be translated to technically better usable standard quantities, especially the gross calorific value H and the density ρ.

The spectral vector, which is derived from the transmission spectrum, is hereby determined by the integration of the measured values of the extinction of the transmission spectrum, in which these integrals are only determined in selected spectral regions. The spectral vector is tuned in correspondence to the usual components included in the composition of the probe gas to be examined. Therefore, the spectral vector is characteristic for the composition of the probe gas in the specific operating state in question. Because the operating state of the probe gas is a not insignificant influence to the transmission spectrum of the probe gas, this factor of influence is taken into consideration in determining the transmission spectrum in the operating state of the probe gas by means of the factor vectors, which are determined by calibration measurements of spectral vectors of definite calibration gases, whose composition and therefore the nominal transmission spectrum is known. These factor vectors are determined by simultaneous measurement of the present state conditions, so that the influence of temperature T and pressure p of the transmission spectrum of calibration gases is known. These factor vectors can therefore be carried out by scalar multiplying, which is simple to carry out and needs no iteration steps, with the spectral vector determined by means of simple mathematical operations. With respect to the quantity to be determined according to the quality of gas, a correlated factor vector derived from the calibration measurement can be brought in. Therefore a high accuracy with this procedure according to the invention can be obtained for a broad region of the state of the probe gas, in which the influence of the quantities of the state can be compensated.

A first embodiment of the invention provides that the factor vectors are determined in advance in a definite measurement environment by means of calibrating measurements, which are carried out with calibrating gases of known features and under known conditions of state. Such a definite measurement environment offers as well the possibility to determine the transmission spectrum being the base of the calculation of the factor vectors as well as the state quantities temperature T and pressure p with a high accuracy, which can not be obtained by carrying out the procedure in the field with arguable costs. The factor vectors are highly accurate correction values for the influence of the measurement of the transmission by the operating state of the probe gas, in which the factor vectors can be determined three-dimensional and by time separated of the determination of the spectral vectors.

There are advantages, that during the calibrating measurements the factor vectors are determined in the form of a characteristic mapping by the variation of pressure p and temperature T of the used calibrating gases. With this method, it is possible to determine for broad regions of the changes of pressure p and temperature T the according factor vectors in advance and to place them at disposal for the scalar multiplying with the spectral vector. The changes of the transmission spectrum due to the pressure p, the so-called pressure broadening, as also the changes in accordance with the temperature can be taken into consideration.

Furthermore, variations of the operating point of the measuring apparatus according to the operating state of the probe gas can be compensated. These variations occur, for example, in a spectrometer because of the variation of the density of the particles in the area in the measuring beam. Also, real gas effects of the probe gases which behave themselves not as an ideal gas, can be compensated, so that the density of the particles in the area in the measuring beam is not directly proportional to the quotient of pressure p and temperature T. The calibration by means of the calibration gases is caused by a series of definite operating states in a phase field and for a suitable set of calibrating gases, so that as a result, a factor vector characteristic mapping (p,T) for each measuring quantity is obtainable, that is fixed by the quantity of operating.states pressure p and temperature T.

There is a special advantage, if for each of the physical quantities to be determined in respect to the quality of gas, a respective factor vector coming from the characteristic mapping for a state of the probe gas is determined. Figuratively speaking, for each of the physical quantities to be determined with respect to the quality of gas derived from the characteristic mapping (p,T), a projection onto the respective plane of the quantity to be determined is carried out, so that for each quantity to be determined, an especially resulting factor vector can be determined.

Because of the connection of the quantity of operating states pressure p and temperature T during the recording of the spectral vector, there is a further advantage, if, for constituting the scalar product with the respective according spectral vector that factor vector is chosen from the characteristic mapping, which corresponds to the state quantities of the probe gas during the recording of the spectrum of the probe gas and to the physical quantity to be determined with respect of the quality of gas. By means of this assignment of the factor vector to the quantities of operating states pressure p and temperature T of the probe gas, a considerable compensation of the influence of the quantities of operating states to the transmission spectrum takes place.

Also it is conceivable, that for each physical quantity to be determined with respect to the quality of gas, at least one spectral vector has to be constituted, in which the so constituted spectral vectors can be constituted from values coming from spectral regions with different boundary wavelengths and/or different sizes of spectral regions and/or a different numbers of spectral regions. With respect to the physical quantity to be determined with respect of the quality of gas, it can be advantageous to determine appropriate adapted spectral vector, because spectral regions adapted respectively to their position and magnitude in the spectrum or their number allow a higher accuracy of the measurement, as it would be possible with similar spectral regions for all physical quantities to be determined with respect to the quality of gas. Therefore, in a further development for the constitution of every physical quantity to be determined with respect to the quality of gas, different spectral regions can be brought in.

Also it important that the number and position of the spectral regions of each scalarly multiplied spectral vector and factor vector correspond to each other. Only in this way a physically correct result can be obtained, so that during determination of the characteristic mapping of the factor vectors a series of characteristic mappings is to be determined with spectral vectors which are based respectively on other spectral regions.

A special preferred embodiment of the procedure according to the invention provides that for the determination of the physical quantity to be determined with respect of the quality of gas, a separation formulation is carried out, in which one part of the physical quantity to be determined is varied essentially with the composition of the probe gas and another part is influenced only slightly by the state of the probe gas and by the composition of the probe gas. The part which is influenced by the state of the probe gas can be calculated by means of determined state data coming from a known average gas, whereas the part which varies essentially with the composition of the probe gas is determined from the transmission spectrum of the probe gas. By means of this separation into two parts according to the separation formulation it is possible to increase the accuracy of the determination of the physical quantity to be determined with respect of the quality of gas.

In a first embodiment, the physical quantity to be determined with respect to the quality of gas, the compressibility coefficient K of the probe gas can be determined. A further embodiment provides that as the physical quantity to be determined with respect to the quality of gas, the compressibility factor Z of the probe gas is determined. Also it is conceivable, that as the physical quantity to be determined with respect of the quality of gas, the density R of the probe gas and/or the Wobbe index Wv and/or the methane factor and/or the molar mass and/or the dew point of the probe gas is determined.

In a further embodiment it is conceivable, that as physical quantity to be determined with respect of the quality of gas, the density of the part of carbon dioxide of the probe gas is determined, from which afterwards by usage of the directly determined real gas behaviour, for example the compressibility coefficient K or the real gas factor Z, the mol fraction $XCO_2$ can be calculated, that means the quota of $CO_2$-molecules in the probe gas. Therewith also the density of carbon dioxide in an operating state can be translated to the appropriate carbon dioxide mol fraction $XCO_2$. This $CO_2$-concentration, which is needed in procedures of conventional gas measuring techniques as one of the input values for the calculation of the compressibility coefficient K, for example, according to the procedure SGERG, can also be determined due to reasonable compatibility by means of the procedure according to the invention. Also, it is possible with this measuring of the absorption due to carbon dioxide $CO_2$ derived from the transmission spectrum, to obtain an increase of the measuring accuracy of the other quantities to be determined with respect to the quality of gas, because they deliver further information about the mixture of the not burnable components of typical probe gases such as nitrogen and carbon dioxide.

There is a special advantage if the transmission spectrum of the probe gas is recorded in the region of infrared light, preferably in the region of the near-infrared. In this spectral region, radiation sources, detectors and further optical components are cheap and deliverable on the market in high numbers and high quality, so that the needed measurement techniques for carrying out the procedures can be constructed inexpensively.

A first embodiment provides, that as spectral regions at least parts of the transmission spectrum in the region between about 1550 nm and 2050 nm are used. A capture of the influences of the probe gas to the transmission spectrum in selected sections of such a broad spectral region allows a considerable adaptation and tuning of the procedure according to the invention to respective probe gases in question, which can be influenced within the bounds of calibration measurement for determination of the factor vectors.

In a further embodiment, as the spectral region for the determination of the part of methane $CH_4$, which can be found proportionally most frequently in burnable gases, radiation at about 1620 to 1660 nm is usable, in which these and the following data of the spectral regions shall be emphasized only as preferred and by means of practical measuring most effective spectral regions. It is directly to be understood, the in case of other compositions of gas or other managing of processes in between of the previously mentioned regions other or further spectral regions can be elected. For the determination of the parts of the sum of all aliphatic hydrocarbons as the spectral region, radiation at about 1670 to 1770 nm can be used. Also it is conceivable, that for the determination of the part of carbon dioxide $CO_2$, radiation at about 2000 to 2020 nm can be used. The preceding values for the spectral regions all lie in a region of the first harmonic overtone band of the molecule oscillations and offer therefore special fine conditions for a correct capture of the quantities to be determined with respect to the quality of gas. Of course, measurements can be carried out in the region of further overtone oscillations, but also of the fundamental wave.

During the constitution of the scalar product, a correcting function is included, which takes into consideration the equipment differences between the measurement arrangement during the determination of the factor vectors with the calibrating gases and the measurement arrangement during the determination of the spectral vector of the probe gas. Such a correcting function takes into consideration the equipment differences between a high-accuracy calibration measurement arrangement and the measurement arrangements designed for practical usage, which must, besides scatter because of technical equipment, make cuts in accuracy. Therefore in the scope of calibrating each single apparatus, which is determined for the implementation of the procedure according to the invention, it is adjusted, and differences between the respective apparatus and the calibration measurement which exist, is taken into consideration as a correcting factor for the results of the determination of the transmission spectrum. By this, it is also always guaranteed in the case of manufacturing of respective apparatuses in series production, that a difference resulting from the series production is captured and can be compensated. Calibration is divided into master-calibration and specimen-calibration: With a master-specimen of the measuring apparatus typical for a design, a measurement of respective spectral vectors is carried out in a wide field of well defined states and a suitable set of well-defined calibration gases and there form the calculation of the respective factor vectors. The determination of the spectral apparatus constant of the single serial specimen of the design is then carried out via measurement of only one or a less amount of calibration gases and comparison of the difference to the respective master-calibration.

There is a special advantage, that as source for the radiation penetrating the probe gas during the recording of the transmission spectrum broadband, radiators, especially thermal radiators, can be used. The radiators capture the transmission spectrum by usage of interference filters and/or a monochromator and/or optical detectors and prepare it in the sense of measuring techniques in such a manner, that the input values for the procedure according to the invention can be derived. It can also be conceivable, that as a source for the radiation penetrating the probe gas during the recording of the transmission spectrum, narrow-band radiators, especially light-emitting diodes (LED) or sources of laser light, are used, if their spectral characteristics can be suitably adjusted.

A further simplification of the procedure according to the invention is obtainable, if the boundary wavelength of the chosen spectral regions during the recording of the transmission spectrum are determined by means of appointing the boundary wavelength relative to a reference signal. While recording the spectrums according the procedure in question, the spectral position of the bands relative to the boundaries of the chosen spectral regions have a great influence for the accuracy of the evaluation. In common laboratory spectrometers as typical measurement arrangements, the absolute accuracy of wavelength is guaranteed by means of a high expenditure with respect to the mechanical workmanship and by usage of reference wavelengths (interference filters, laser). For avoiding this high technical expenditure for series arrangements, the absolute position of the wavelength can be determined by means of a characteristic position of the reference signal and corrected reference to the axis of the wavelength. In case of analyzing, for example, natural gas as probe gas, in a further development as a reference signal, the region of the best absorption of the radiation of methane, the so-called absorption peak of methane at about 1666 nm is offered. This maximum is best qualified for the correction, because methane as guiding component always dominates in natural gas and the high coefficient of extinction of this maximum allows for good detection. The position of this maximum is evaluated and, relative to this maximum, the position of the boundary wavelengths of the chosen spectral regions are adjusted. With this, the requirements for the absolute accuracy of the wavelength of respective measurement arrangements can be reduced substantially. The resulting error of wavelength depends rather on the limited reproducibility of the wavelength adjustment. In a further development it is conceivable, that alternatively as reference signal typical gradients of spectrums of mediums are used, which are placed additionally in the beam path of the arrangement for measuring the transmission spectrum, as this can be carried out in the form of plastic foils, that are placed in the reference beam path of the measuring arrangement.

A further increase of the accuracy of the procedure according to the invention can be obtained, if among other spectral regions, in which the transmission spectrum of the probe gas contains information about its composition, spectral regions are surveyed, in which no absorption by the probe gas occurs. Such a survey of additional spectral regions is important during the practical usage of the measurement arrangement in respect of the long-time stability, because there may be variations in the blank transmission of the measuring channel, which are not established because of changes of the probe gas and therefore falsify the measurement result. The spectral regions which are not or not as much influenced by the composition of the probe gas therefore can, in a further development, be used for the self-control of the measurement of the probe gas in the form of a reference, in which in a first embodiment for calibration of the measurement arrangement essentially at every recording of a transmission spectrum of the probe gas or in a frequent succession a measurement in the absorption free spectral region of the probe gas is carried out. For these purposes, for example, at each recording of a spectrum region also an absorption free spectral region can be recorded, in which the measurement arrangement after the recording of the spectral regions carried out with the procedure according to the invention again carries out a measurement in the region not depending on the spectral region of the probe gas and compares the therein determined transmission with the respective latest measurement in this spectral region. If such a change in transmission in a region not depending on the spectral region of the probe gas goes beyond a given limit, than in further development a blank measurement of the measuring arrangement with a absorption free spectral region for, e.g., natural gas can be carried out to compensate for the measurement conditions. In this way, an automatic self control of the measuring system can be carried out.

Another embodiment provides that the difference of at least one of the preceding measurements underneath a given threshold value is taken into consideration as correction factor for the measurements for the determination of the physical quantities to be determined according to the quality of gas. In this way, an improvement of the measuring results during the actual usable measurement can be obtained by the evaluation of the determined differences.

A very advantageous spectral region for the transmission in general independent of the composition of the probe gas is positioned in the region of about 1500 to 1600 nm.

A further embodiment provides, that one or several of the physical quantities to be determined according to the quality of gas are determined only by means of calculation by usage of quantities derived from the transmission spectrum by constitution of the scalar product in such a manner. The physical quantities determined via measurement and calculation describe and essentially correct the real gas behaviour of the probe gas by the way of inserting them in standardized approximate methods. For example the transmission spectrum for the measuring of the part of $CO_2$ in the probe gas is evaluated in a region above 2000 nm, so expensive and fault susceptible sensors are needed, which allow measurements in this high region of wavelength. Such sensors cost more than measuring equipment in the region up to 1800 nm, so that the necessary measuring arrangement for carrying out the procedure according to the invention with incorporation of the part of $CO_2$ is significantly more expensive as a measuring arrangement, for example, if only for the capture of burnable gases of a probe gas.

For establishing a compatibility with apparatuses of the common techniques for measuring gases, the part of carbon dioxide in the probe gas can be determined only by calculation in such a way, that using the procedure according to the invention the real gas behaviour and further physical quantities to be determined according to the quality of gas are determined by the scalar product of the spectral vector and factor vector. The component, which is not determined with measuring techniques, for example the part of carbon dioxide, can be calculated from the quantities derived as described above in such a way, that by means of reversal of a standardized procedure as for example the procedure SGERG or the same after application of the respective procedure results in the correct real gas behaviour. With the procedure according to the invention, a sufficiently exact determination of the quota of carbon dioxide is available, without complicating or making the procedure much more expensive because of its equipment conversion.

What is claimed is:

1. A procedure for determining quality of a probe gas, comprising:
    determining a transmission spectrum of the probe gas at operating conditions by spectroscopical methods of measurement;
    determining pressure p and temperature T of the probe gas;
    determining at least one spectral vector $\overline{S}$ in a number of selected spectral regions by integrating quantities of the transmission spectrum of the probe gas, the spectral vector having as components values of integrals with respect to the selected spectral regions and being characteristic for the properties of the probe gas at operating conditions; and
    multiplying said spectral vector $\overline{S}$ with a factor vector $\overline{V}$, said factor vector $\overline{V}$ determined by calibrating measurements of spectral vectors $\overline{S}$ of calibrating gases having known features and under known conditions, in which a respective factor vector $\overline{V}$ is used to determine a physical quantity based on the quality of the gas, wherein during calibrating measurements, the factor vectors $\overline{V}$ are determined in the form of a characteristic mapping by a variation of pressure p and temperature T of the calibrating gases.

2. The procedure according to claim 1, wherein for each physical quantity to be determined, a respective factor vector $\overline{V}$ coming from the characteristic mapping is determined.

3. The procedure according to claim 1, wherein for multiplying with a respective spectral vector $\overline{S}$, a factor vector $\overline{V}$ is chosen from the characteristic mapping, said factor vector corresponding to the quantities of the probe gas during recording of the spectrum of the probe gas and to the physical quantity to be determined.

4. A procedure for determining quality of a probe gas, comprising:
    determining a transmission spectrum of the probe gas at operating conditions by spectroscopical methods of measurement;
    determining pressure p and temperature T of the probe gas;
    determining at least one spectral vector $\overline{S}$ in a number of selected spectral regions by integrating quantities of the transmission spectrum of the probe gas, the spectral vector having as components values of integrals with respect to the selected spectral regions and being characteristic for the properties of the probe gas at operating conditions; and
    multiplying said spectral vector $\overline{S}$ with a factor vector $\overline{V}$, said factor vector $\overline{V}$ determined by calibrating measurements of spectral vectors $\overline{S}$ of calibrating gases having known features and under known conditions, in which a respective factor vector $\overline{V}$ is used to determine a physical quantity based on the quality of the gas, wherein for each physical quantity to be determined with respect to the quality of the gas, at least one spectral vector $\overline{S}$ must be created from values coming from spectral regions with different boundary wavelengths or different sizes of spectral regions or different numbers of spectral regions.

5. Procedure according to claim 4, wherein different spectral regions are used for every physical quantity to be determined.

6. Procedure according to claim 4, wherein a number and position of the spectral regions of each multiplied spectral vector $\overline{S}$ and factor vector $\overline{V}$ correspond to each other.

7. Procedure according to claim 4, wherein the selected spectral regions comprise at least parts of the transmission spectrum in the region between about 1550 nm and 2050 nm.

8. Procedure according to claim 4, wherein the spectral region for determination of a part comprising methane $CH_4$ radiation is at about 1620 to 1660 nm.

9. Procedure according to claim 4, wherein the spectral region for determination of a part comprising a sum of all aliphatic hydrocarbon radiation is at about 1670 to 1770 nm.

10. Procedure according to claim 4, wherein the spectral region for determination of a part comprising carbon dioxide radiation is at about 2000 to 2020 nm.

11. A procedure for determining quality of a probe gas, comprising:

determining a transmission spectrum of the probe gas at operating conditions by spectroscopical methods of measurement;

determining pressure p and temperature T of the probe gas;

determining at least one spectral vector $\overline{S}$ in a number of selected spectral regions by integrating quantities of the transmission spectrum of the probe gas, the spectral vector having as components values of integrals with respect to the selected spectral regions and being characteristic for the properties of the probe gas at operating conditions; and multiplying said spectral vector $\overline{S}$ with a factor vector $\overline{V}$, said factor vector $\overline{V}$ determined by calibrating measurements of spectral vectors $\overline{S}$ of calibrating gases having known features and under known conditions, in which a respective factor vector $\overline{V}$ is used to determine a physical quantity based on the quality of the gas, wherein a separation formulation is carried out for determining the physical quantity, in which one part of the physical quantity to be determined varies with the state and composition of the probe gas and another part is influenced only slightly by the composition and state of the probe gas.

12. Procedure according to claim 11, wherein the part that is influenced only slightly with the state of the probe gas is calculated by determined state data coming from a known average gas.

13. Procedure according to claim 11, wherein the part that varies with the composition of the probe gas is determined from the transmission spectrum of the probe gas.

14. A procedure for determining quality of a probe gas, comprising:

determining a transmission spectrum of the probe gas at operating conditions by spectroscopical methods of measurement;

determining pressure p and temperature T of the probe gas;

determining at least one spectral vector $\overline{S}$ in a number of selected spectral regions by integrating quantities of the transmission spectrum of the probe gas, the spectral vector having as components values of integrals with respect to the selected spectral regions and being characteristic for the properties of the probe gas at operating conditions; and multiplying said spectral vector $\overline{S}$ with a factor vector $\overline{V}$, said factor vector $\overline{V}$ determined by calibrating measurements of spectra vectors $\overline{S}$ of calibrating gases having known features and under known conditions, in which a respective factor vector $\overline{V}$ is used to determine a physical quantity based on the quality of the gas, wherein the physical quantity comprises a compressibility coefficient K of the probe gas.

15. A procedure for determining quality of a probe gas, comprising:

determining a transmission spectrum of the probe gas at operating conditions by spectroscopical methods of measurement;

determining pressure p and temperature T of the probe gas;

determining at least one spectral vector $\overline{S}$ in a number of selected spectral regions by integrating quantities of the transmission spectrum of the probe gas, the spectral vector having as components values of integrals with respect to the selected spectral regions and being characteristic for the properties of the probe gas at operating conditions; and multiplying said spectral vector $\overline{S}$ with a factor vector $\overline{V}$, said factor vector $\overline{V}$ determined by calibrating measurements of spectral vectors $\overline{S}$ of calibrating gases having known features and under known conditions, in which a respective factor vector $\overline{V}$ is used to determine a physical quantity based on the quality of the gas, wherein the physical quantity to be determined comprises a compressibility factor Z of the probe gas.

16. A procedure for determining quality of a probe gas, comprising:

determining a transmission spectrum of the probe gas at operating conditions by spectroscopical methods of measurement;

determining pressure p and temperature T of the probe gas;

determining at least one spectral vector $\overline{S}$ in a number of selected spectral regions by integrating quantities of the transmission spectrum of the probe gas, the spectral vector having as components values of integrals with respect to the selected spectral regions and being characteristic for the properties of the probe gas at operating conditions; and multiplying said spectral vector $\overline{S}$ with a factor vector $\overline{V}$, said factor vector $\overline{V}$ determined by calibrating measurements of spectral vectors $\overline{S}$ of calibrating gases having known features and under known conditions, in which a respective factor vector $\overline{V}$ is used to determine a physical quantity based on the quality of the gas, wherein the physical quantity to be determined comprises a density $\rho$ of the probe gas.

17. A procedure for determining quality of a probe gas, comprising:

determining a transmission spectrum of the probe gas at operating conditions by spectroscopical methods of measurement;

determining pressure p and temperature T of the probe gas;

determining at least one spectral vector $\overline{S}$ in a number of selected spectral regions by integrating quantities of the transmission spectrum of the probe gas, the spectral vector having as components values of integrals with respect to the selected spectral regions and being characteristic for the properties of the probe gas at operating conditions; and multiplying said spectral vector $\overline{S}$ with a factor vector $\overline{V}$, said factor vector $\overline{V}$ determined by calibrating measurements of spectral vectors $\overline{S}$ of calibrating gases having known features and under known conditions, in which a respective factor vector $\overline{V}$ is used to determine a physical quantity based on the quality of the gas, wherein the physical quantity to be determined comprises a Wobbe index of the probe gas.

18. A procedure for determining quality of a probe gas, comprising:

determining a transmission spectrum of the probe gas at operating conditions by spectroscopical methods of measurement;

determining pressure p and temperature T of the probe gas;

determining at least one spectral vector $\overline{S}$ in a number of selected spectral regions by integrating quantities of the transmission spectrum of the probe gas, the spectral vector having as components values of integrals with respect to the selected spectral regions and being characteristic for the properties of the probe gas at operating conditions; and multiplying said spectral vector $\overline{S}$ with a factor vector $\overline{V}$, said factor vector $\overline{V}$ determined by calibrating measurements of spectral vectors $\overline{S}$ of calibrating gases having known features and under known conditions, in which a respective factor vector $\overline{V}$ is used to determine a physical quantity based on the quality of the gas, wherein the physical quantity to be determined is a methane factor of the probe gas.

19. A procedure for determining quality of a probe gas, comprising:

determining a transmission spectrum of the probe gas at operating conditions by spectroscopical methods of measurement;

determining pressure p and temperature T of the probe gas;

determining at least one spectral vector $\overline{S}$ in a number of selected spectral regions by integrating quantities of the transmission spectrum of the probe gas, the spectral vector having as components values of integrals with respect to the selected spectral regions and being characteristic for the properties of the probe gas at operating conditions; and multiplying said spectral vector $\overline{S}$ with a factor vector $\overline{V}$, said factor vector $\overline{V}$ determined by calibrating measurements of spectral vectors $\overline{S}$ of calibrating gases having known features and under known conditions, in which a respective factor vector $\overline{V}$ is used to determine a physical quantity based on the quality of the gas, wherein the physical quantity to be determined is the molar mass of the probe gas.

20. A procedure for determining quality of a probe gas, comprising:

determining a transmission spectrum of the probe gas at operating conditions by spectroscopical methods of measurement;

determining pressure p and temperature T of the probe gas;

determining at least one spectral vector $\overline{S}$ in a number of selected spectral regions by integrating quantities of the transmission spectrum of the probe gas, the spectral vector having as components values of integrals with respect to the selected spectral regions and being characteristic for the properties of the probe gas at operating conditions; and multiplying said spectral vector $\overline{S}$ with a factor vector $\overline{V}$, said factor vector $\overline{V}$ determined by calibrating measurements of spectral vectors $\overline{S}$ of calibrating gases having known features and under known conditions, in which a respective factor vector $\overline{V}$ is used to determine a physical quantity based on the quality of the gas, wherein the physical quantity to be determined is the density of a carbon dioxide part of the probe gas.

21. A procedure for determining quality of a probe gas, comprising:

determining a transmission spectrum of the probe gas at operating conditions by spectroscopical methods of measurement;

determining pressure p and temperature T of the probe gas;

determining at least one spectral vector $\overline{S}$ in a number of selected spectral regions by integrating quantities of the transmission spectrum of the probe gas, the spectral vector having as components values of integrals with respect to the selected spectral regions and being characteristic for the properties of the probe gas at operating conditions; and multiplying said spectral vector $\overline{S}$ with a factor vector $\overline{V}$, said factor vector $\overline{V}$ determined by calibrating measurements of spectral vectors $\overline{S}$ of calibrating gases having known features and under known conditions, in which a respective factor vector $\overline{V}$ is used to determine a physical quantity based on the quality of the gas, wherein the physical quantity to be determined is the dew point of the probe gas.

22. A procedure for determining quality of a probe gas, comprising:

determining a transmission spectrum of the probe gas at operating conditions by spectroscopical methods of measurement;

determining pressure p and temperature T of the probe gas;

determining at least one spectral vector $\overline{S}$ in a number of selected spectral regions by integrating quantities of the transmission spectrum of the probe gas, the spectral vector having as components values of integrals with respect to the selected spectral regions and being characteristic for the properties of the probe gas at operating conditions; and multiplying said spectral vector $\overline{S}$ with a factor vector $\overline{V}$, said factor vector $\overline{V}$ determined by calibrating measurements of spectral vectors $\overline{S}$ of calibrating gases having known features and under known conditions, in which a respective factor vector $\overline{V}$ is used to determine a physical quantity based on the quality of the gas, wherein during said step of multiplying, a correcting function is included, said correcting function taking into account equipment differences between a measurement arrangement during determination of the factor vectors $\overline{V}$ with the calibrating gases and a measurement arrangement during determination of the spectral vector $\overline{S}$ of the probe gas.

23. Procedure according to claim 18, wherein the measurement arrangement of the spectral vector $\overline{S}$ of the probe gas is gauged for one time and results are set in accordance with respective results of the measuring arrangement during recording of the factor factors $\overline{V}$ with the calibrating gases.

24. A procedure for determining quality of a probe gas, comprising:

determining a transmission spectrum of the probe gas at operating conditions by spectroscopical methods of measurement;

determining pressure p and temperature T of the probe gas;

determining at least one spectral vector $\overline{S}$ in a number of selected spectral regions by integrating quantities of the transmission spectrum of the probe gas, the spectral vector having as components values of integrals with respect to the selected spectral regions and being characteristic for the properties of the probe gas at operating conditions; and multiplying said spectral vector $\overline{S}$ with a factor vector $\overline{V}$, said factor vector $\overline{V}$ determined by calibrating measurements of spectral vectors $\overline{S}$ of calibrating gases having known features and under known conditions, in which a respective factor vector $\overline{V}$ is used to determine a physical quantity based on the quality of the gas, wherein a boundary wavelength of chosen spectral regions during recording of the transmission spectrum is determined by appointing the boundary wavelength relative to a reference signal.

25. Procedure according to claim 24, wherein a characteristic signature of the transmission spectrum to be recorded is used as the reference signal.

26. Procedure according to claim 24, wherein typical gradients of spectrums of mediums are used as the reference signal, said gradients being placed additionally in a beam path of an arrangement for measuring the transmission spectrum.

27. A procedure for determining quality of a probe gas, comprising:

determining a transmission spectrum of the probe gas at operating conditions by spectroscopical methods of measurement;

determining pressure p and temperature T of the probe gas;

determining at least one spectral vector $\overline{S}$ in a number of selected spectral regions by integrating quantities of the transmission spectrum of the probe gas, the spectral vector having as components values of integrals with respect to the selected spectral regions and being characteristic for the properties of the probe gas at operating conditions; and multiplying said spectral vector $\overline{S}$ with a factor vector $\overline{V}$, said factor vector $\overline{V}$ determined by calibrating measurements of spectral vectors $\overline{S}$ of calibrating gases having known features and under known conditions, in which a respective factor vector $\overline{V}$ is used to determine a physical quantity based on the quality of the gas, wherein among spectral regions in which the transmission spectrum of the probe gas contains information about the composition of the probe gas, other spectral regions are surveyed in which very little or no absorption by the gas probe occurs.

28. Procedure according to claim 27, wherein the spectral regions in which very little or no absorption occurs are used for self-control of the measurement of the probe gas in the form of a reference.

29. Procedure according to claim 27, wherein the spectral regions in which very little or no absorption occurs are positioned in an area of about 1500 to 1600 nm.

* * * * *